United States Patent
Hassidov et al.

(10) Patent No.: US 10,646,108 B2
(45) Date of Patent: May 12, 2020

(54) ANCILLARY VACUUM MODULE USABLE WITH AN ENDOSCOPE

(71) Applicant: Motus GI Medical Technologies Ltd., Tirat HaCarmel (IL)

(72) Inventors: Noam Hassidov, Moshav Bustan HaGalil (IL); Eyal Kochavi, Haifa (IL); Tzach Arnon, Yodfat (IL); Kobi Luleko, Eshchar (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 0 days.

(21) Appl. No.: 15/107,512

(22) PCT Filed: Dec. 24, 2014

(86) PCT No.: PCT/IL2014/051124
§ 371 (c)(1),
(2) Date: Jun. 23, 2016

(87) PCT Pub. No.: WO2015/097703
PCT Pub. Date: Jul. 2, 2015

(65) Prior Publication Data
US 2016/0317000 A1 Nov. 3, 2016

Related U.S. Application Data

(60) Provisional application No. 61/920,499, filed on Dec. 24, 2013.

(51) Int. Cl.
*A61B 1/015* (2006.01)
*A61B 1/018* (2006.01)
(Continued)

(52) U.S. Cl.
CPC .......... *A61B 1/015* (2013.01); *A61B 1/0014* (2013.01); *A61B 1/00068* (2013.01);
(Continued)

(58) Field of Classification Search
CPC ............ A61B 1/00089; A61B 1/00094; A61B 1/00119; A61B 1/00128; A61B 1/00131;
(Continued)

(56) References Cited

U.S. PATENT DOCUMENTS 4,971,034 A * 11/1990 Doi ..................... A61B 1/00068
600/104
5,279,542 A 1/1994 Wilk
(Continued)

FOREIGN PATENT DOCUMENTS

| JP | 62-261354 | 11/1987 |
| JP | 11-216104 | 8/1999 |

(Continued)

OTHER PUBLICATIONS

Supplementary European Search Report and the European Search Opinion Dated Aug. 8, 2017 From the European Patent Office Re. Application No. 14874579.7. (6 Pages).

(Continued)

*Primary Examiner* — Ryan N Henderson

(57) ABSTRACT

According to some embodiments of the invention there is provided a colon cleaning system comprising: a working channel, a vacuum source, a separate vacuum pipe provided alongside the working channel, and a sensor positioned at a conduit connected externally to the working channel, the sensor configured for providing an indication related to pressure within at least a segment of the working channel. In some embodiments, the system comprises a controller configured for controlling one or more parameters of a vacuum induced in the separate vacuum pipe, the parameter determined according to the pressure related indication provided by the sensor.

10 Claims, 10 Drawing Sheets

(51) Int. Cl.
*A61B 1/31* (2006.01)
*A61B 1/00* (2006.01)
*A61M 1/00* (2006.01)
*A61B 1/12* (2006.01)

(52) U.S. Cl.
CPC ...... *A61B 1/00094* (2013.01); *A61B 1/00135* (2013.01); *A61B 1/018* (2013.01); *A61B 1/12* (2013.01); *A61B 1/126* (2013.01); *A61B 1/31* (2013.01); *A61M 1/0035* (2014.02); *A61B 1/00137* (2013.01); *A61M 1/0025* (2014.02); *A61M 2210/1064* (2013.01)

(58) Field of Classification Search
CPC .............. A61B 1/00137; A61B 1/0014; A61B 1/00142; A61B 1/012; A61B 1/015; A61B 1/126–128; A61B 1/31; A61B 1/317; A61B 1/12; A61M 1/0023; A61M 1/0025; A61M 1/0027; A61M 1/0029; A61M 1/0031; A61M 1/0033; A61M 1/0035; A61M 2210/106; A61M 2210/1064; A61M 2210/1067
See application file for complete search history.

(56) References Cited

U.S. PATENT DOCUMENTS

| | | | |
|---|---|---|---|
| 5,630,795 A | 5/1997 | Kuramoto et al. | |
| 5,788,650 A | 8/1998 | Dotolo | |
| 6,309,346 B1* | 10/2001 | Farhadi | A61B 1/00156 600/114 |
| 6,641,553 B1 | 11/2003 | Chee et al. | |
| 7,066,880 B2* | 6/2006 | Wendlandt | A61B 1/00156 600/114 |
| D536,449 S | 2/2007 | Nakajima et al. | |
| 2003/0187460 A1* | 10/2003 | Chin | A61B 17/00008 606/129 |
| 2004/0092960 A1* | 5/2004 | Abrams | A61B 17/0686 606/139 |
| 2004/0133149 A1 | 7/2004 | Haischmann et al. | |
| 2006/0052666 A1 | 3/2006 | Kumar et al. | |
| 2006/0079861 A1 | 4/2006 | Matasov | |
| 2006/0116586 A1* | 6/2006 | Sekiguchi | A61B 1/0005 600/470 |
| 2006/0235458 A1 | 10/2006 | Belson | |
| 2007/0015965 A1 | 1/2007 | Cox et al. | |
| 2007/0179432 A1 | 8/2007 | Bar Or et al. | |
| 2007/0191678 A1* | 8/2007 | Sekiguchi | A61M 25/1018 600/116 |
| 2007/0198000 A1 | 8/2007 | Miyamoto et al. | |
| 2007/0244363 A1* | 10/2007 | Sano | A61B 1/00039 600/158 |
| 2008/0146876 A1* | 6/2008 | Noguchi | A61B 1/00068 600/118 |
| 2008/0294008 A1* | 11/2008 | Toyama | A61B 1/015 600/139 |
| 2009/0062611 A1* | 3/2009 | Toyama | A61B 1/00082 600/118 |
| 2009/0143722 A1 | 6/2009 | Kim | |
| 2009/0187069 A1* | 7/2009 | Terliuc | A61B 1/00142 600/106 |
| 2010/0125165 A1* | 5/2010 | Torii | A61B 1/00045 600/106 |
| 2010/0256447 A1 | 10/2010 | Dubi et al. | |
| 2010/0292536 A1* | 11/2010 | Yamakawa | A61B 1/00094 600/116 |
| 2010/0298773 A1 | 11/2010 | Nitsan et al. | |
| 2011/0105845 A1* | 5/2011 | Gordon | A61B 1/00094 600/156 |
| 2011/0105846 A1* | 5/2011 | Yoshie | A61B 1/0053 600/158 |
| 2012/0101336 A1 | 4/2012 | Hirsch et al. | |
| 2012/0289892 A1* | 11/2012 | Shtul | A61B 1/31 604/28 |
| 2012/0289910 A1* | 11/2012 | Shtul | A61M 3/0241 604/267 |
| 2013/0066297 A1* | 3/2013 | Shtul | A61M 3/0241 604/514 |
| 2013/0085442 A1* | 4/2013 | Shtul | A61B 1/015 604/28 |
| 2013/0303852 A1* | 11/2013 | Hiraga | A61B 1/015 600/118 |
| 2014/0005479 A1* | 1/2014 | Loske | A61B 1/015 600/115 |
| 2015/0257633 A1* | 9/2015 | Hassidov | A61B 1/00089 600/127 |
| 2016/0206805 A1* | 7/2016 | Hassidov | A61M 1/0031 |
| 2017/0087284 A1* | 3/2017 | Shtul | A61B 1/12 |

FOREIGN PATENT DOCUMENTS

| | | |
|---|---|---|
| JP | 2004-000601 | 1/2004 |
| JP | 2010-005091 | 1/2010 |
| JP | 2010-063483 | 3/2010 |
| JP | 2010-063774 | 3/2010 |
| JP | 2011-518584 | 6/2011 |
| JP | 2011-520567 | 7/2011 |
| JP | 2016-533830 | 11/2016 |
| WO | WO 92/17219 | 10/1992 |
| WO | WO 99/60934 | 12/1999 |
| WO | WO 2005/117685 | 12/2005 |
| WO | WO 2006/039511 | 4/2006 |
| WO | WO 2008/093288 | 8/2008 |
| WO | WO 2008/155776 | 12/2008 |
| WO | WO 2009/000346 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/027109 | 3/2010 |
| WO | WO 2010/138521 | 12/2010 |
| WO | WO 2015/029039 | 3/2015 |
| WO | WO 2015/097703 | 7/2015 |

OTHER PUBLICATIONS

International Preliminary Report on Patentability dated Jul. 7, 2016 From the International Bureau of WIPO Re. Application No. PCT/IL2014/051124.
International Search Report and the Written Opinion dated Apr. 2, 2015 From the International Searching Authority Re. Application No. PCT/IL2014/051124.
Supplementary European Search Report and the European Search Opinion dated Apr. 10, 2019 From the European Patent Office Re. Application No. 18214285.1. (8 Pages).
Notice of Reasons for Rejection dated Sep. 4, 2018 From the Japan Patent Office Re. Application No. 2016-538539 and Its Translation Into English. (7 Pages).
Decision to Grant A Patent dated Nov. 27, 2018 From the Japan Patent Office Re. Application No. 2016-538539 and Its Translation Into English. (4 Pages).

* cited by examiner

ANCILLARY VACUUM MODULE USABLE WITH AN ENDOSCOPE

RELATED APPLICATIONS

This application is a National Phase of PTC patent Application No. PCT/IL 2014/051124 having International filing date of Dec. 24,2014, which claims the benefit of priority under 35 USC § 119(e) of U.S. Provisional Patent Application No. 61/920,499 filed on Dec. 24,2013. The contents of the above applications are all incorporated by reference as if fully set forth in their entirety.

FIELD AND BACKGROUND OF THE INVENTION

The present invention, in some embodiments thereof, relates to an ancillary module usable with an endoscope and, more particularly, but not exclusively, to a vacuum module external to a colonoscope, governed by indications related to pressure within at least a segment of the colonoscope.

Many existing systems for endoscopic exploration and treatment of the lower intestinal tract use an endoscope having working channels used to irrigate the colon and to extract fecal matter which obscures view of and access to the colon tissue. As the working channels of standard endoscopes are often too narrow to provide efficient evacuation of fecal matter, it is not unusual for such channels to become clogged with matter. Such clogging requires the physician or other practitioner to interrupt the procedure, retract the endoscope from its inserted position in the colon, and to purge or otherwise clean the working channel, and then reinsert the endoscope to continue the interrupted procedure.

Several piping systems external to a colonoscope have been disclosed in prior art, for example:

International Patent Publication No. WO2009/143201 A1 to Gordon et al. teaches "A method for enhancing performance of an endoscope (212) for use with a body lumen that has not been sufficiently cleaned for viewing with the endoscope (212), including assembling an endoscopic device (100, 400) to an endoscope (212), the endoscopic device (100, 400) including a washing member (201, 404) that provides a flow of cleaning fluid for cleaning a body lumen, and a suction member (206, 406) for draining material from the body lumen, and causing fluid to exit the washing member (201, 404) into the body lumen to clear debris away from a path of the endoscope (212) so that the endoscope (212) can view the exposed body lumen, and draining at least a portion of the debris through the suction member (206, 406)."

International Patent Publication No. WO2010/138521 A3 to Hirsch et al. teaches "An endoscopic system for use with an endoscope, including an irrigation tube that provides a flow of irrigation fluid for cleaning a body lumen, and a suction tube for sucking material from the body lumen, wherein the suction tube is connected to a branch connector and one branch of the branch connector is connected to a suction source tube which is connected to a suction source and another branch of the branch connector is connected to a vent tube, and wherein the suction source tube and the vent tube pass through a double pinch valve".

U.S. Pat. No. 5,630,795 to Oaki et al. teaches "A cleaning tube apparatus for an endoscope, comprises the endoscope having an observation optical system for observing a subject part at a forward-end portion, a cleaning tube detachable with respect to said endoscope, said cleaning tube being provided with a plurality of fluid jetting openings in a peripheral direction at one end of said cleaning tube, said fluid jetting openings being provided for leading cleaning fluid at least to said observation optical system, and a fluid supply unit connected to said cleaning tube, for supplying the cleaning fluid to said cleaning tube."

SUMMARY OF THE INVENTION

According to an aspect of some embodiments of the present invention, there is provided a colon cleaning system comprising: a working channel of a colonoscope; a vacuum source, functionally coupled to the working channel; a vacuum pipe, the vacuum pipe being positioned outside the colonoscope and alongside the working channel; a conduit configured to remain outside the human body, the conduit connected to the working channel; and a sensor positioned in the conduit and configured to provide an indication related to pressure within at least a segment of the working channel; a controller configured for controlling at least one parameter of a vacuum induced in the separate vacuum pipe, the at least one parameter being determined according to the pressure related indication provided by the sensor.

According to some embodiments of the invention, the at least one parameter of the induced vacuum includes at least one of timing, intensity, and frequency.

According to some embodiments of the invention, the controller is configured to control at least one of an intensity and timing of the induced vacuum in the separate vacuum pipe.

According to some embodiments of the invention, the induced vacuum is strong enough to evacuate at least one of fecal matter and fluid from the colon.

According to some embodiments of the invention, the controller comprises a user interface through which a user can select an operation mode.

According to an aspect of some embodiments of the present invention, there is provided the system, further including three operation modes, comprising: (a) a mode in which induction of vacuum in the separate vacuum pipe is restricted and vacuum is induced solely in the working channel; (b) a mode in which the controller determines the at least one parameter of the induced vacuum in the separate vacuum pipe according to the pressure related indication provided by the sensor; and (c) a mode in which vacuum is induced in the separate vacuum pipe independently of the pressure related indication.

According to some embodiments of the invention, the system comprises a vacuum control valve included in the colonoscope, the vacuum control valve being operable to control the application of vacuum to the working channel from the vacuum source, and wherein application of vacuum within the separate vacuum pipe is activated by operation of the vacuum control valve.

According to an aspect of some embodiments of the present invention, there is provided the system, further including three operation modes, comprising: (a) a mode in which induction of vacuum in the separate vacuum pipe is restricted and vacuum is induced solely in the working channel; (b) a mode in which operation of the vacuum control valve induces vacuum in the separate vacuum pipe; and (c) a mode in which vacuum is induced in the separate vacuum pipe independently of the vacuum control valve.

According to some embodiments of the invention, activation of the vacuum control valve induces a coupling of pressure between the conduit and the working channel for detecting pressure changes in the working channel via the conduit.

According to some embodiments of the invention, the vacuum control valve is manually operated.

According to some embodiments of the invention, the colonoscope comprises a Y-junction, wherein a first branch of the Y-junction comprises a portion of the working channel and a second branch of the Y-junction comprises a removable cap.

According to some embodiments of the invention, the removable cap comprises an orifice configured to receive a tool for insertion into the working channel.

According to some embodiments of the invention, walls of the orifice fit tightly around the tool so that vacuum breaching in the working channel is not affected by the orifice.

According to some embodiments of the invention, the system comprises a blocking element insertable into the second branch of the Y-junction, and advanceable into the working channel to a position where it hermetically seals a distal portion of the working channel, so that vacuum induced in a proximal portion of the working channel is not transmitted to a distal end of the channel.

According to some embodiments of the invention, the blocking element comprises an inflatable balloon.

According to some embodiments of the invention, the colonoscope is configured so that activation of the vacuum control valve during operation results in an increased vacuum in the working channel, and reduced pressure in the conduit connected thereto.

According to some embodiments of the invention, the decrease in pressure in the conduit is sensed by the sensor, and the sensor signals the controller to induce increased vacuum within the separate vacuum pipe.

According to some embodiments of the invention, the functional coupling of the vacuum source to the working channel comprises the conduit extending between the working channel and the vacuum source.

According to some embodiments of the invention, vacuum provided by the vacuum source is modified by a vacuum regulator.

According to some embodiments of the invention, the vacuum is modified according to a difference between the pressure-related indication and a predefined pressure indication profile.

According to some embodiments of the invention, the sensor detects at least one of a change in pressure, and an absolute pressure.

According to some embodiments of the invention, the system comprises a collection tank configured for separating gas from liquid and solid matter conducted by at least one of the separate vacuum pipe and the working channel.

According to some embodiments of the invention, the system comprises a foot pedal that is activated by a user to induce vacuum in the separate vacuum pipe.

According to an aspect of some embodiments of the present invention, there is provided a colon cleaning system comprising: a working channel of a colonoscope; a vacuum source; and a separate pipe, the pipe being positioned outside the colonoscope and alongside the working channel; the separate pipe being configured for at least one of evacuating fecal matter and fluid from the colon, and for delivering a tool into the colon.

According to some embodiments of the invention, the tool is configured for removing a polyp from the colon.

According to some embodiments of the invention, the system comprises a rigid tube within the separate pipe through which the tool is delivered.

According to an aspect of some embodiments of the present invention, there is provided a method for inducing vacuum in a separate vacuum pipe provided alongside a working channel of a colonoscope, comprising: activating a vacuum control valve of the colonoscope; detecting a change in pressure within a conduit connected externally to the working channel; and inducing a vacuum within the separate vacuum pipe to evacuate fecal matter.

According to some embodiments of the invention, the activating a vacuum control valve comprises coupling between the conduit and the working channel.

According to some embodiments of the invention, the inducing a vacuum comprises inducing a relatively stronger vacuum in the separate vacuum pipe when a relatively greater reduction in pressure is detected in the conduit, and inducing relatively weaker vacuum in the separate vacuum pipe when a relatively smaller reduction in pressure is detected in the conduit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
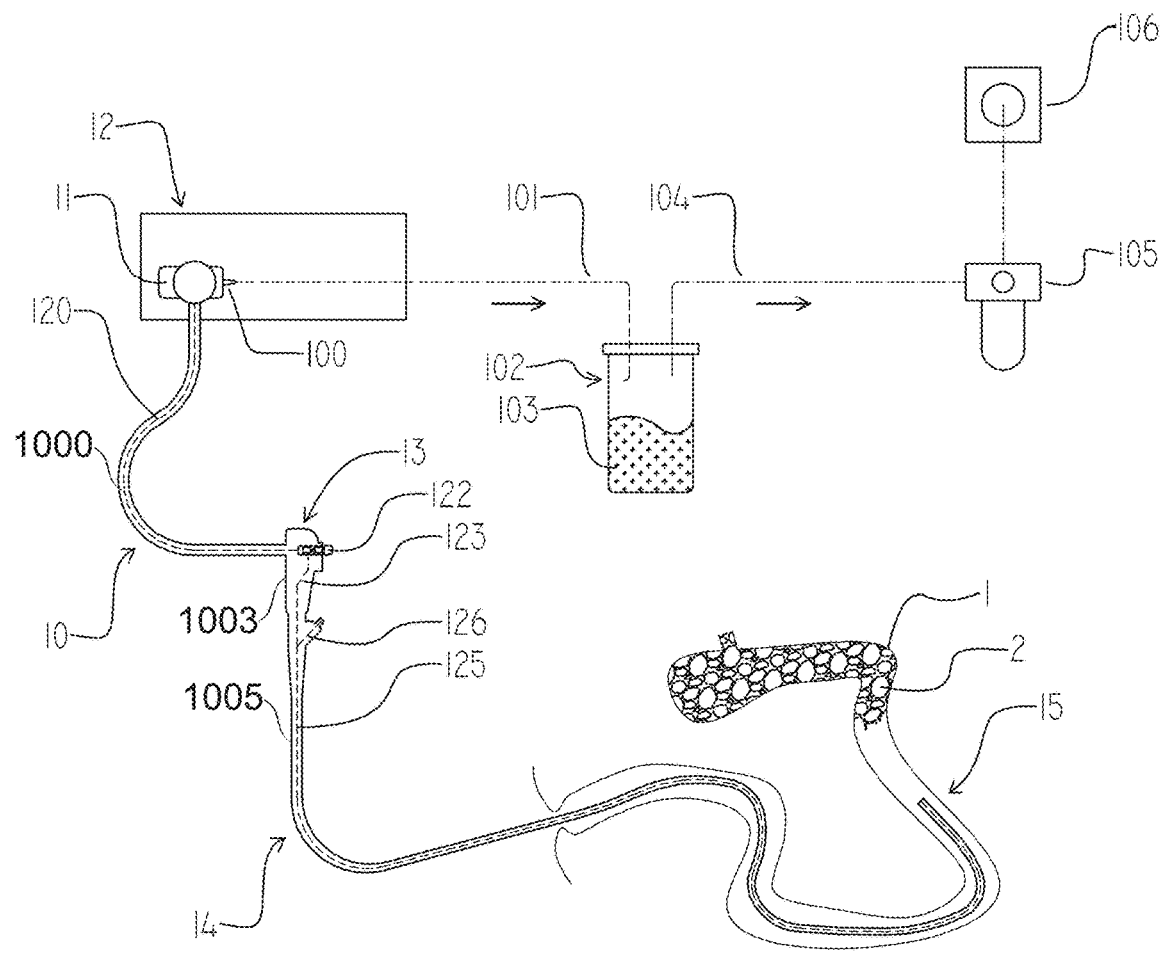
FIG. 1A illustrates an exemplary colon cleaning system commonly used in a colonoscopy procedure, according to some embodiments of the invention.

The present invention, in some embodiments thereof, relates to an ancillary module usable with an endoscope and, more particularly, but not exclusively, to a vacuum module external to a colonoscope, governed by indications related to pressure within at least a segment of the colonoscope.

Overview

A general aspect of some embodiments of the invention relates to a user interface of a colon cleaning system, in which a selectively performed action leads to a secondary action which may assist in carrying out a colonoscopy procedure. Optionally, one or more changes in the system are detected, for example following an action such as activation of a valve, causing a secondary action, such as induction of vacuum, to take place.

An aspect of some embodiments of the invention relates to a colon cleaning system comprising a separate pipe extending along at least a portion of a working channel of a colonoscope. In some embodiments, vacuum is induced in the separate pipe based on a pressure related indication. The word "vacuum" includes induced pressure gradients of, for example, 230-250 mbar, 60-85 mbar, 50-150 mbar, 100-500 mbar, 300-400 mbar, 600-800 mbar, 200-300 mbar, and/or another pressure in a range having the same, larger, smaller, and/or intermediate bounds. Optionally, the pressure related indication is provided by a sensor configured at a conduit connected to the working channel. In some embodiments, the conduit is positioned, at least in part, externally to the human body. In some embodiments, a correlation exists between the pressure level of the working channel and the pressure level in the conduit. Optionally, a pressure level in the conduit effectively depends on a pressure level within at least a portion of the working channel. In some embodiments, the pressure related indication comprises a change in pressure and/or an absolute pressure measurement. In some embodiments, an inner diameter of the conduit ranges between, for example, 2-10 mm, such as 4 mm, 6 mm, 8 mm or an intermediate, longer or shorter diameter. In some embodiments, a length of the conduit ranges between, for example, 10-100 cm, or another longer or shorter length as required to connect the vacuum source with the working channel (and/or any intermediate plumbing), such as 30 cm, 50 cm, 80 cm, 100 cm, or another intermediate, longer or shorter length.

In some embodiments, parameters of the vacuum induced in the separate vacuum pipe and/or within the working channel such as timing, intensity and/or frequency of the vacuum are determined according to the pressure indication. Optionally, the parameters are modified in real time. Optionally, the parameters are selected according to a calibration table, which, for example, matches between vacuum intensities and/or frequencies to a level of detected pressure. In some embodiments, a controller is configured for receiving a signal from the pressure sensor and applying vacuum having parameters set according to the signal. In some embodiments, a vacuum regulator modulates the intensity of the applied vacuum, for example according to a signal provided by the controller. In some embodiments, a controller comprises an electronic controller, the controller being in an enclosure together with the pressure sensor and/or pressure regulating apparatus, and/or separate, and in functional connection to the pressure sensor and/or pressure regulating apparatus. In some embodiments, a controller comprises a mechanical apparatus, whereby a sensed pressure in the conduit is transduced (for example, by motion of a mechanical pressure sensor) into the position of a valve or regulator member, whereby a pressure in the separate vacuum pipe is modified.

In some embodiments, the ancillary vacuum module is activated by a vacuum control valve of a colonoscope. Optionally, the vacuum control valve is activated by a user (e.g. a physician). Additionally or alternatively, the vacuum control valve is automatically activated, for example by a controller. Optionally, the vacuum control valve is activated in situations in which evacuation of fecal matter, fluid and/or gas is required, for example for emptying a clogged working channel and/or for clearing up a colon region in proximity to a distal opening of the working channel. In some embodiments, the vacuum control valve is moved into a position in which a connection is provided, through direct or indirect coupling, between the working channel and the conduit along which the pressure sensor is positioned. Optionally, the pressure level in the conduit changes as a result of connecting the conduit to the working channel. For example, the pressure level in the conduit may decrease, indicating that the vacuum valve has been activated. Optionally, when a coupling between the working channel and the conduit is provided, the pressure level in the conduit changes as a result of a pressure level within at least a segment of the working channel.

In some embodiments, vacuum is induced in the separate vacuum pipe to provide additional evacuation ability to the system. In some embodiments, vacuum is applied simultaneously in the separate vacuum pipe and in the working channel. Alternatively, evacuation of matter is provided only by the separate vacuum pipe. Alternatively, evacuation of matter is provided only by the working channel.

An aspect of some embodiments relates to a blocking element configured for separating between portions of a working channel, such as a distal portion and a proximal portion of the working channel. In some embodiments, the blocking element seals a distal portion of the working channel, so that vacuum does not breach through to the distal portion of the working channel. Optionally, the blocking element is inserted into the working channel to reduce and/or prevent from a working channel that is clogged by fecal matter to affect the pressure indication provided by the sensor. A potential advantage of the insertable blocking element may include maintaining a proper functioning of the system, in which upon identifying a certain pressure indication or a pressure range would apply vacuum in the separate vacuum pipe, for example to clear up a colon region in proximity to a distal opening of the working channel. In some embodiments, the blocking element is inserted through a branch of a Y-junction of the colonoscope's pipeline. Optionally, the blocking element comprises an inflatable balloon.

In some embodiments, the separate pipe provides an additional pathway leading into the colon. Optionally, the separate pipe is sized and/or shaped and/or positioned (e.g. relative to the working channel) to deliver one or more tools, such as a tool for polyp removal, to a colon region. In some embodiments, an additional tube, optionally formed of a rigid material, is inserted through the pipe, for example to permit delivery of a tool without damaging a wall of the pipe.

As used herein, the proximal and distal ends of the colonoscope system are defined as follows: the distal end of the system is configured for insertion into the body, while the proximal end includes system components configured for manipulation by a user, which are positioned externally to the body, and/or the portions of the system closer to a power source such as a wall socket or a wall vacuum inlet. Orientation of other components described herein is defined with respect to the proximal and distal ends of the system.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

For purposes of better understanding some embodiments of the present invention, as illustrated in FIGS. 2-10 of the drawings, reference is first made to the construction and operation of a standard colonoscope system, as illustrated for example in FIG. 1A.

Figure 1B:
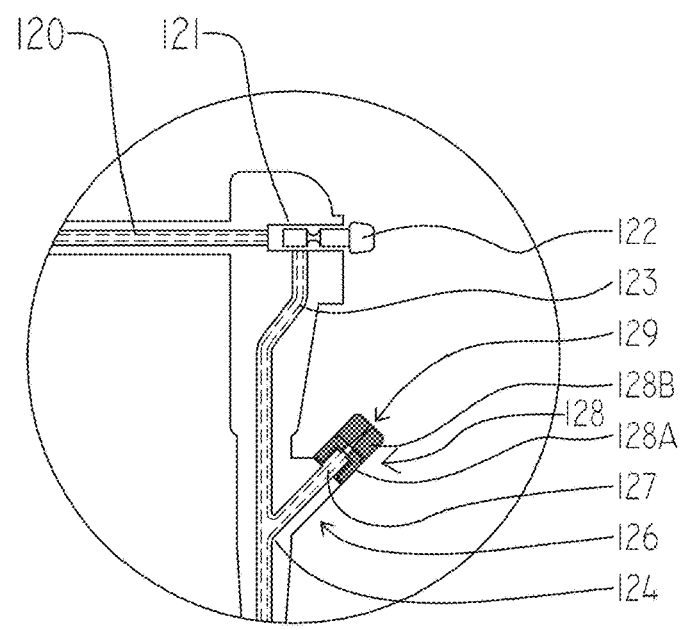
FIG. 1B illustrates an enlarged view of a Y-junction of a colonoscope, according to some embodiments of the invention.

FIG. 1A illustrates a colon cleaning system, commonly used in a colonoscopy procedure. The system comprises a colonoscope 10, connected by a plug 11 to a working station 12. Colonoscope 10 comprises a first section 1001, (commonly referred to as the umbilical cable of a colonoscope) extending between the colonoscope vacuum inlet 100 and a housing 13 of a vacuum valve 122, a second section 1003 extending between valve housing 13 and Y-junction 124 (shown in enlarged view in FIG. 1B), and a third section 1005, extending between Y-junction 124 and a distal end 15 of the colonoscope. A working channel comprising portion 125 (which extends along section 1005) and portion 123 (which extends along section 1003) is passed within the colonoscope's external tube 14 and is typically used to remove fluids and solid matter out of the body using suction, or alternatively used to insert surgical tools into the colon, for example tools for collecting a biopsy sample. An internal pipe 120 extends within section 1001, and is configured to connect to the working channel as will be further described.

Distal end 15 and/or at least a portion of section 1005 of the colonoscope is configured for insertion into a colon 1. The distal end 15 comprises a port leading to the working channel, through which fecal matter, fluid and/or gas such as air are evacuated using vacuum. The evacuated matter is drawn from the body via working channel portion 125, through working channel portion 123, through pipe 120, and then through pipe 101 to reach tank 102. In tank 102, fluid and/or fecal matter 103 are separated from the gas, and the gas (air) is drawn via a secondary pipe 104 to a vacuum regulator 105, through a wall inlet 106 and to a main vacuum source (not shown in this figure). Examples of vacuum sources, their regulation, and operational parameters for inducing a pressure differential through a pipe, channel, conduit, and/or other structure having a lumen are described, for example, in relation to "Exemplary pressure ranges and operation parameters", hereinbelow.

Vacuum valve 122 is operated in the following manner: valve 122 is linearly movable within housing 13, and is configured to connect between pipe 120 and working channel portion 123 when pushed into the housing. During standard operation, valve 122 is not pushed in, and relatively low vacuum levels exist at the distal end of the working channel. When the physician pushes valve 122, for example when a segment of the working channel is clogged, an increased vacuum level is induced, and fecal matter, fluid and gas are evacuated to external tank 102.

Y-junction 124 comprises a side branch 126, dimensioned for insertion of tools into the working channel, such as tools for performing a biopsy, or for removal of polyps. According to some embodiments of the invention, the opening of side branch 126 is covered by a cap 128 comprising two sections: a base section 128A positioned on top of the opening of side branch 126, and a removable section 128B. Removable section 128B comprises an orifice 129 for insertion of tools. When the opening of side branch 126 is exposed (i.e. not covered by removable section 128B), pushing valve 122 will not generate vacuum within the working channel, or generate insignificant vacuum that does not have an effect on evacuating fecal matter.

Figure 2:
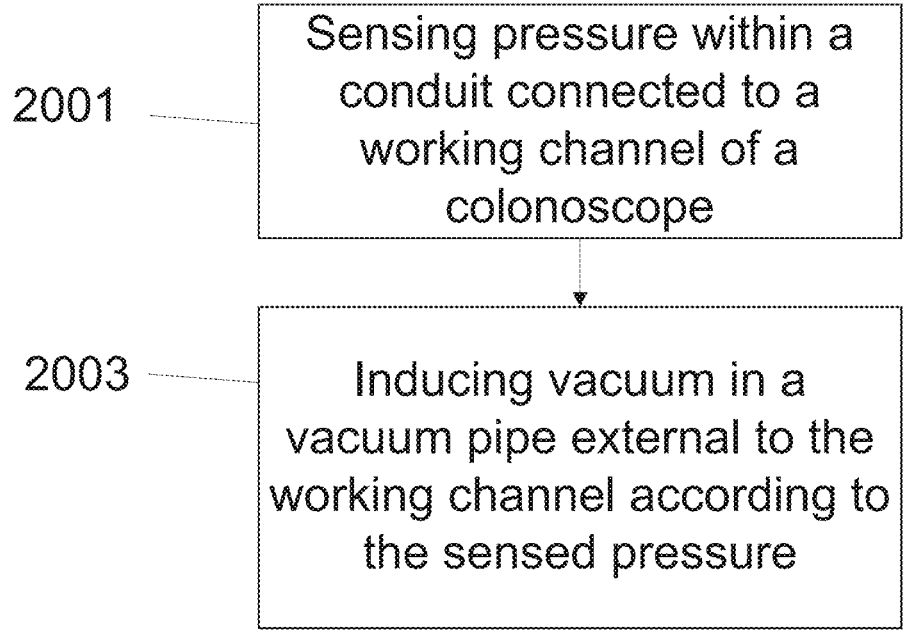
FIG. 2 is a flowchart of a method for inducing vacuum in a separate pipe provided alongside a working channel of a colonoscope, according to some embodiments of the invention.

FIG. 2 is a flowchart of a general method for inducing vacuum in a vacuum pipe positioned externally to a colonoscope, according to some embodiments of the invention.

In some embodiments, being positioned externally to a colonoscope comprises being positioned at least partially alongside and externally to a colonoscope probe, for example as described hereinbelow in relation to block 2003, and/or in relation to FIG. 4 for vacuum pipe 200 and colonoscope external tube 14.

In some embodiments, the method comprises sensing pressure within a conduit positioned externally to the body, the conduit being connected to a working channel of a colonoscope (at block 2001). For example, as also described in relation to FIG. 4, a conduit 220A comprises a conduit connected to working channel 123, 125, and a sensor 211 is positioned to sense pressure within the conduit 220A.

In some embodiments, the connection forms a passage between the lumens of the conduit and the working channel. Optionally, gas (such as air), fluid and/or fecal matter are permitted to pass through the connection. In some embodiments, the connection comprises a valve, for example providing a full or partial obstruction of the passageway between the lumens of the conduit and the working channel. In some embodiments, the connection comprises valve 122.

In some embodiments, a pressure level in the conduit is detected by a sensor, such as an electronic pressure sensor. Optionally, the sensor is configured for detecting pressure levels within the conduit, for example pressure levels ranging between 5-700 mbar, such as 50, 150, 200, 250 mbar or intermediate, larger or smaller levels.

In some embodiments, the sensor is configured for indicating pressure over time, for example indicating a rising pressure level, a descending pressure level, or a constant pressure level.

In some embodiments, the pressure measurement is made relative to ambient pressure, for example atmospheric pressure (gauge pressure). Additionally or alternatively, the sensor is configured for detecting absolute pressure levels, measured in reference to a complete vacuum.

In some embodiments, the pressure level in the conduit changes as a function of the pressure level in at least a segment of the working channel. Optionally, the pressure level in the conduit changes as a function of opening or closing a valve (for example, valve 122) configured between the working channel and the conduit. Optionally, the pressure level in the conduit is higher when the valve is closed (i.e. the valve is in a configuration that does not connect between the lumens of the conduit and the working channel), and lower when the valve is open. Optionally, the pressure level in the conduit changes in response to clogging of the working channel, for example by fecal matter.

In some embodiments, the method comprises inducing vacuum in a separate vacuum pipe (at block 2003). In some embodiments, the pipe is positioned externally to the working channel, for example extending alongside at least a portion of the working channel, to be inserted into the body adjacent the working channel. Under certain conditions, the separate pipe is configured to provide the colonoscope with additional suction abilities for evacuating fecal matter and/or fluid and/or gas from the intestinal tract. In some embodiments, vacuum is induced in the separate pipe according to the pressure sensed at the conduit external to the body. Optionally, vacuum parameters such as the timing of the vacuum, the intensity applied, the duration of activation are determined according the pressure indication measured at the conduit. In some embodiments, a frequency of the vacuum is determined. In some embodiments, a phase of the applied wave is selected, for example the selected phase can be opposite from a vacuum and/or pressure wave through the working channel, for example for intentionally forming a turbulence within the colon which may assist in breaking fecal matter.

Alternatively, in some embodiments, a distally directed pressure wave is applied through the separate pipe (i.e. opposite to the direction of vacuum), for example for pushing away fecal matter and/or causing it to break.

In some embodiments, the pressure indication which activates the vacuum module comprises a predetermined value (for example 200 mbar), or a pressure range (e.g. 100-250 mbar). Optionally, the vacuum module is activated above or below a pressure threshold, for example, below a pressure level of 50 mbar, 60 mbar, 30 mbar or intermediate, higher or lower thresholds.

Figure 3:
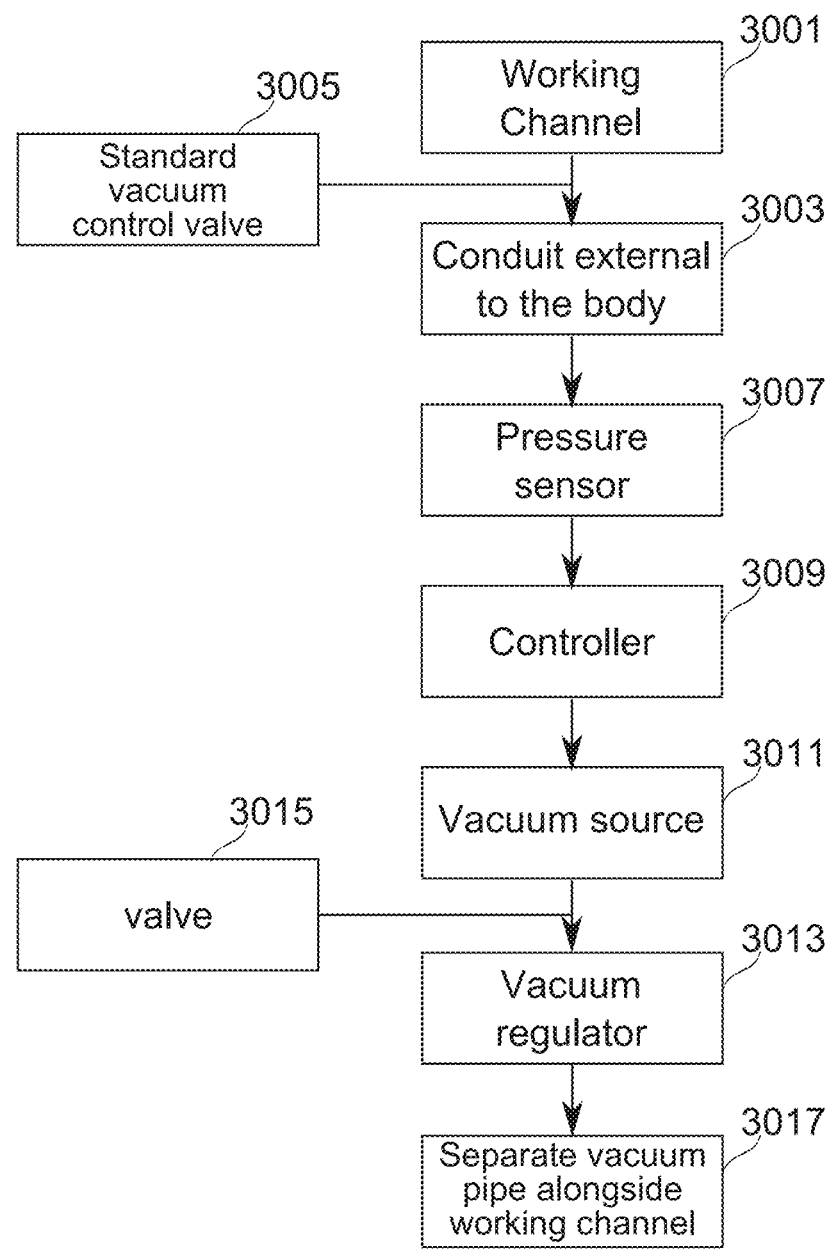
FIG. 3 is a block diagram of components of a colon cleaning system comprising an ancillary vacuum module, according to some embodiments of the invention.
Figure 6:
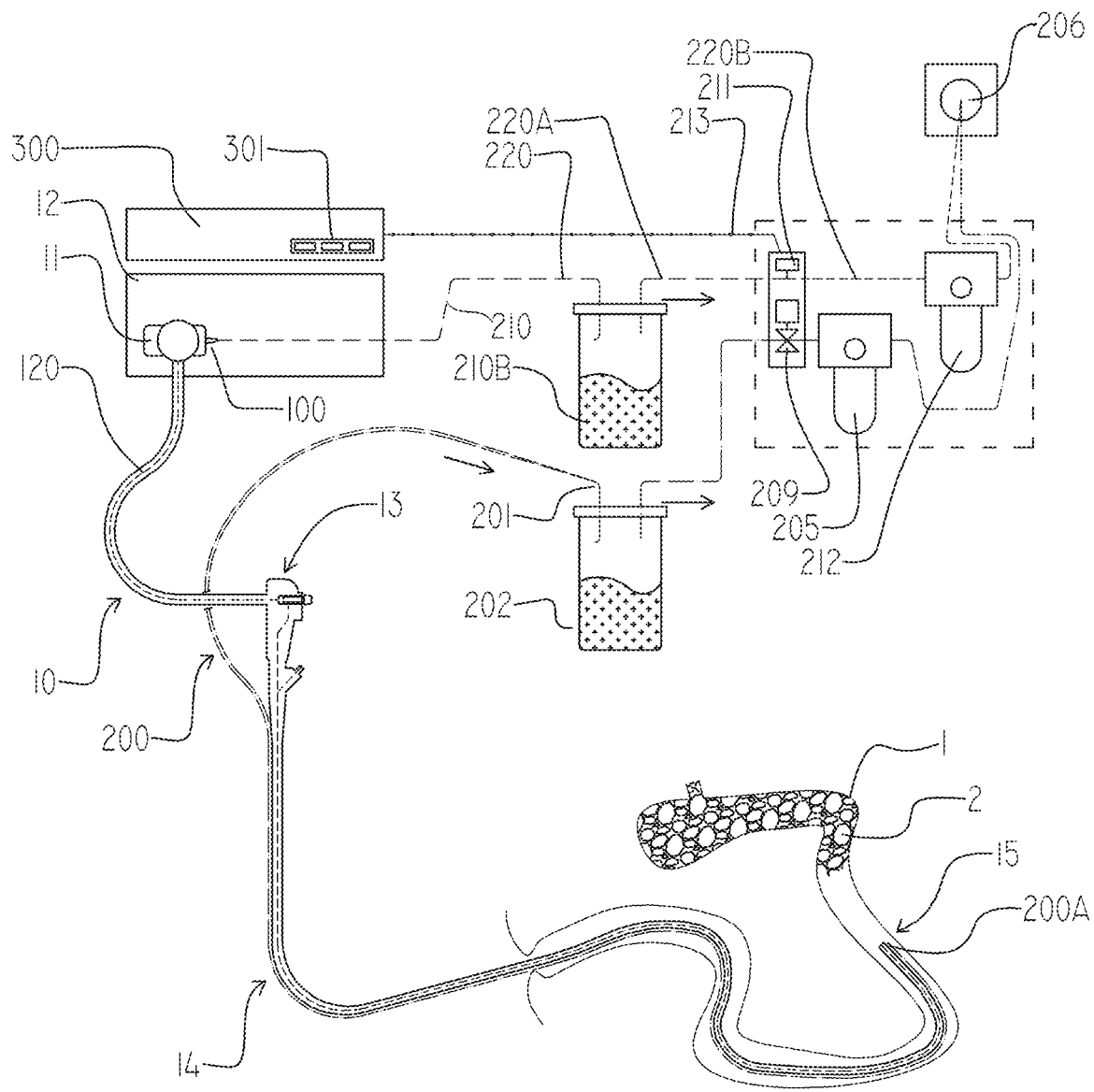
FIG. 6 is an illustration of a colon cleaning system comprising a separate vacuum pipe governed by indications related to pressure within at least a segment of the working channel of a colonoscope, according to some embodiments of the invention.

FIG. 3 is a block diagram of components of a colon cleaning system comprising an ancillary vacuum module, according to some embodiments of the invention. In some embodiments, the system comprises a working channel 3001 configured for insertion, at least in part, into the colon (for example, having a length such that it reaches to a distal end of the colon, for example as shown in FIGS. 1A, 4, and 6). In some embodiments, the working channel is connected, directly or through an additional channel, to a conduit 3003 positioned externally to the body. Optionally, a connection between the working channel and the conduit comprises a vacuum control valve 3005, which, in some embodiments, may be a standard control valve of a colon cleaning system, as shown for example in the prior art described by FIGS. 1A-B (valve 122).

In some embodiments, a pressure sensor 3007 is configured to measure the pressure level, such as gas pressure, at conduit 3003. Optionally, the sensor is configured at a distal end (e.g. closer to the working channel), a proximal end (e.g. closer to a vacuum source), at a center of the conduit, or at other locations along the conduit. Optionally, sensor 3007 is positioned at a wall of conduit 3003. Alternatively, sensor 3007 is positioned within a lumen of conduit 3003. Optionally, a plurality of sensors such as 2, 3, 4 or more sensors, used for detecting pressure at a plurality of sections of the conduit.

In some embodiments, sensor 3007 is in electrical communication with a controller 3009, for example connected through a wiring connection. Alternatively, the connection between controller 3009 and sensor 3007 is a wireless connection. In some embodiments, controller 3009 is comprised within a workstation, which may further comprise a user interface to present and/or acquire data from a user, as further described herein. Optionally, the user interface is configured to present the pressure level detected by the sensor on a screen.

In some embodiments, controller 3009 is configured for inducing and/or modifying vacuum applied in separate pipe 3017 which is configured alongside the working channel. Optionally, vacuum is generated by a vacuum source 3011, for example being a hospital wall vacuum inlet, an electrical pump or a peristaltic pump. In some embodiments, the vacuum source which generates vacuum for the separate pipe is configured for generating vacuum for the working channel of the colonoscope as well. Alternatively, two or more vacuum sources are used, for example one source generates vacuum within the separate pipe, and a second source generates vacuum within the working channel.

In some embodiments, the vacuum generated by vacuum source 3011 is modified by a vacuum regulator 3013. Optionally, a valve 3015 such as a solenoid valve is positioned between the vacuum source 3011 and the vacuum regulator 3013.

In some embodiments, controller 3009 is configured for setting and/or modifying parameters of the induced vacuum according to the pressure indication provided by the sensor. In some embodiments, valve 3015 is transferred to an open position by receiving a signal from controller 3009, permitting vacuum (which can be considered as back pressure to flow to the vacuum regulator, which in turn modifies the intensity of the vacuum induced in the separate pipe 3017. In some embodiments, vacuum regulator 3013 is calibrated to provide certain vacuum intensities in response to one or more signals provided by the controller 3009. In some embodiments, the vacuum intensities are set by a user, such as a physician, for example during operation. Additionally or alternatively, the vacuum levels are set automatically by controller 3009, for example according to a calibration table which links, for example, between the pressure related indication measured at conduit 3003 and the vacuum intensity that is induced at separate pipe 3017.

Figure 4:
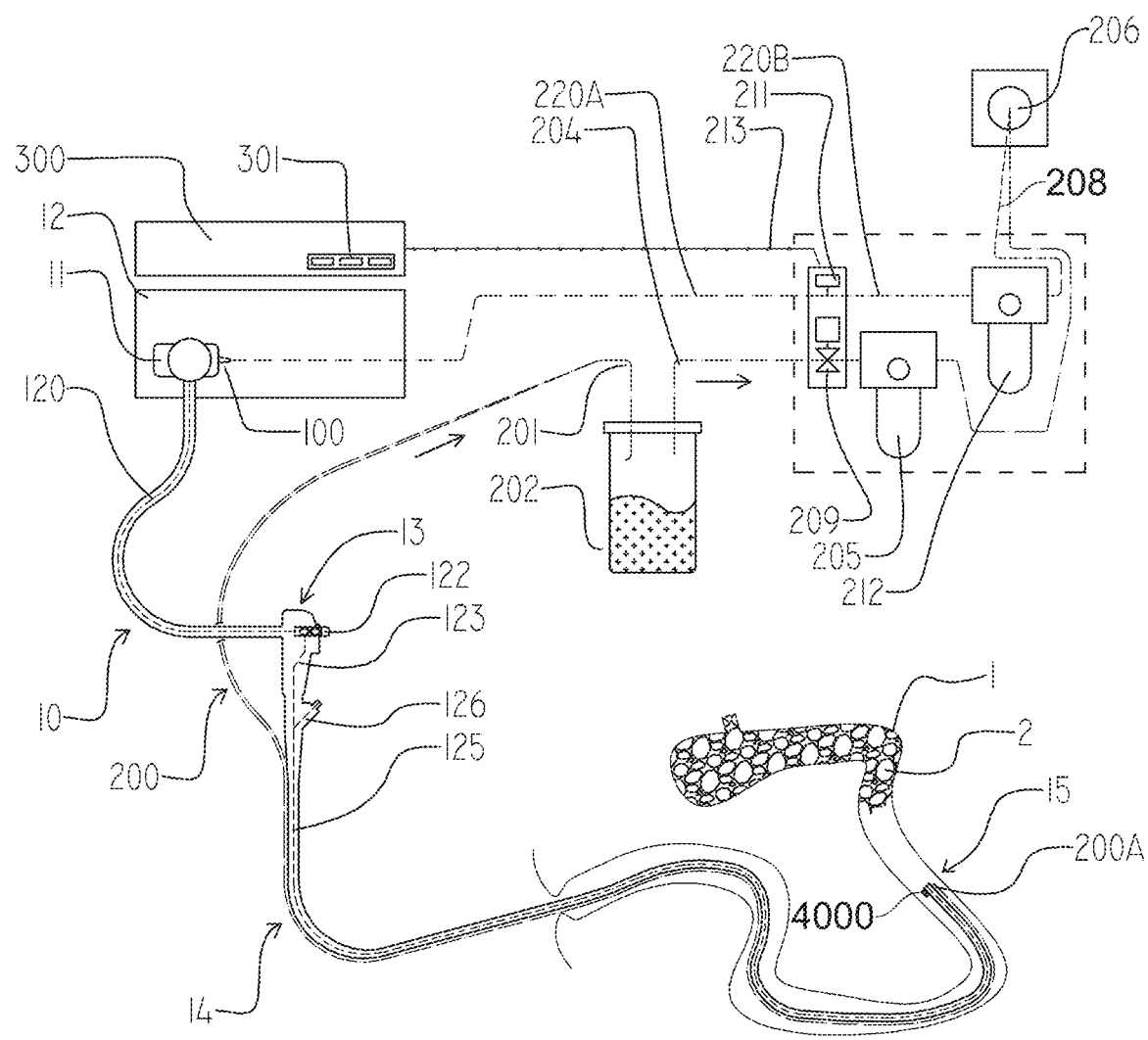
FIG. 4 is an illustration of a colon cleaning system comprising a separate vacuum pipe governed by indications related to pressure within at least a segment of the working channel of a colonoscope, according to some embodiments of the invention.

FIG. 4 is an illustration of a colon cleaning system comprising a separate vacuum pipe governed by indications related to pressure within at least a segment of the working channel of a colonoscope, according to some embodiments of the invention.

The following describes an exemplary operation mechanism of a system as illustrated in FIG. 4, which comprises an ancillary vacuum module. The ancillary vacuum module is comprised of, in this example, a separate vacuum pipe 200, secondary pipes 201 and 204 forming the vacuum supply line to pipe 200, a valve 209, a secondary vacuum regulator 205, a conduit 220A, a pressure sensor 211, an optional collection tank 202, an optional controller 300. It is noted that the ancillary vacuum module is not limited to the listed components and may comprise of only some of the components and/or comprise of additional components, for example a foot pedal for applying and/or ceasing the generation of vacuum.

In some embodiments, applying vacuum in separate vacuum pipe 200 involves a change in a configuration of vacuum valve 122. For clarity, the exemplary mechanism described herein below is referred to in two system configurations: a first state in which valve 122 is pulled back, and a second state in which valve 122 is pushed into its housing.

A Pulled-Back State of the Valve

When valve 122 is configured in its pulled back position, a connection between working channel portion 123 and pipe 120 is prevented, and vacuum is ceased. In some embodiments, during standard operation (i.e. when no vacuum is induced within separate pipe 200), a pressure level in the distal portion 125 of the working channel is relatively low, for example ranging between 60-85 mbar, such as 65 mbar, 75 mbar, 80 mbar or intermediate, higher or lower pressure levels. Optionally, the pressure level in portion 125 of the working channel is constant. Optionally, the pressure level in portion 125 of the working channel is lower than a pressure level within the colon 1. A pressure level in portion 125 that is lower than pressure level within the colon may effectively form vacuum (that is, at least partial vacuum) within portion 125. Optionally, the formed vacuum is relatively weak so that fluid and fecal matter are not drawn into the working channel.

In some embodiments, at the pulled back state of valve 122, relatively high pressure exists within external conduit 220A, extending between the colonoscope's vacuum inlet 100 and vacuum regulator 212. Optionally, this relatively high pressure is formed as a result of preventing or limiting a connection between the lumens of pipe 120 and of working channel portion 123. In some embodiments, the relatively high pressure in conduit 220A at this state ranges between 230-250 mbar, such as 232, 240, 245 mbar, or intermediate, larger or smaller levels. Optionally, the pressure level in the conduit is controlled by vacuum regulator 212, for example being set according to a predetermined, calibrated level. In some embodiments, generation of vacuum is provided by vacuum source 206. Optionally, vacuum source 206 is connected to vacuum regulator 212, which in turn is configured for modifying the intensity of the vacuum generated by vacuum source 206.

In some embodiments, the pressure in conduit 220A is detected by a pressure sensor 211, positioned at the conduit. In some embodiments, sensor 211 is connected, for example via a cable 213, to a controller 300. Optionally, a signal from pressure sensor 211 is sent to the controller.

In some embodiments, the vacuum supply line to separate vacuum pipe 200 comprises, as referred to in the proximal direction, a secondary pipe 201, leading into a tank 202, and a pipe 204, which is connected on its proximal end to a secondary vacuum regulator 205. Optionally, a valve 209, for example a solenoid valve, is configured along pipe 204 to allow and/or to limit the vacuum.

In some embodiments, at the pulled back state of the valve, no vacuum is induced in separate pipe 200. Optionally, at this state, solenoid valve 209 is in a closed configuration which prevents the vacuum from breaching.

A Pushed-In State of the Valve

In some embodiments, for example when working channel portion 125 is clogged by fecal matter, valve 122 is activated, for example pushed (e.g. by a physician)into housing 13 in attempt to create additional vacuum within the working channel, which would evacuate fluid and/or fecal matter. This action may be normally performed (for example in prior art systems) to cause gas and/or fluid to be drawn externally from the body, and optionally flow into a collection tank such as tank 102 shown in FIGS. 1A-B. In some embodiments, when pushed in, valve 122 is configured to allow a connection between working channel portion 123 and pipe 120. Optionally, the coupling between the lumens of working channel portion 123 and pipe 120 reduces the pressure level within conduit 220A. The relatively low pressure, for example ranging between 50-150 mbar, such as 70, 100, 130 mbar or intermediate, larger or smaller pressure levels is sensed by pressure sensor 211, which in turn sends a signal to controller 300. The controller then sends a signal to solenoid valve 209, which transfers into an open configuration, permitting the breaching of vacuum within separate pipe 200 (optionally through secondary pipes 201 and 204). Optionally, by inducing vacuum within separate vacuum pipe 200, evacuation force is provided, and gas, fluid and/or fecal matter are sucked from the colon and conducted by pipe 200 away from the body.

In some embodiments, a distal opening 200A of pipe 200 is positioned adjacent a distal opening of working channel portion 125. Optionally, by inducing vacuum within pipe 200, a colon region in proximity to the openings is cleared, providing, for example, for visualizing of the region using, for example, a camera or other optical device inserted through the colonoscope.

In some embodiments, the parameters of the vacuum induced in separate pipe 200 are determined according to the pressure indication provided by sensor 211. Optionally, the parameters are modified according to changes in the measured pressure, for example in real time. In some embodiments, the controller is configured for setting a timing, an intensity, a duration, and/or a frequency of the induced vacuum. In some embodiments, vacuum is introduced in pulses.

In some embodiments, in the pushed-in state of valve 122, the pressure in conduit 220A effectively depends on the pressure within portion 123 of the working channel. Additionally or alternatively, the pressure in conduit 220A is a function of the pressure within portion 125 of the working channel. Optionally, a pressure at least a portion of the working channel, such as portion 123 and/or 125 can be deduced from the pressure related indication provided by sensor 211. When deducing the pressure, an intensity of the vacuum induced in the system (for example a constant vacuum induced in the system) may be taken into consideration.

In some embodiments, the intensity of the vacuum applied is proportional to a change in pressure, such as a decrease in pressure. For example, relatively stronger vacuum is induced in separate pipe 200 when a relatively greater reduction in pressure is detected in conduit 220A, and relatively weaker vacuum is induced in separate pipe 200 when a smaller reduction in pressure is detected in conduit 220A.

In some embodiments, an intensity of the applied vacuum is modified according to a difference between detected pressure and a predefined pressure profile which may be defined in a calibration table.

In some embodiments, the pressure level within separate pipe 200 when vacuum is induced ranges between, for example, 100-500 mbar, such as 200 mbar, 350 mbar, 450 mbar on intermediate, higher or lower pressure levels.

In some embodiments, vacuum is applied gradually, for example according to a positioning of valve 122. Optionally, valve 122 is operated in a linear manner so that the intensity of the vacuum induced in pipe 200 increases with the advancement of valve 122 into housing 13. For example, in some embodiments, valve 122 can be partially pushed-in, inducing vacuum at an intensity lower than the intensity provided when valve 122 is fully pushed in. Optionally, when valve 122 is fully pushed in, the pressure indication ranges between 300-400 mbar, such as 320, 350, 370 mbar or intermediate, higher or lower pressure levels.

A potential advantage of providing suction abilities or additional suction abilities to the colonoscope by inducing vacuum within separate vacuum pipe 200 may include reducing and/or preventing situations in which the procedure is interrupted, for example for clearing the working channel and/or valve 122 from fecal matter which clogged them.

Fluid Collecting Tank

In some embodiments, tank 202 provides for separating between gas, such as air, and liquid, which were evacuated through separate pipe 200. Additionally or alternatively, fecal matter is collected within tank 202. Optionally, separation between liquid and gas utilizes gravitational forces, causing the fluid to accumulate at the bottom of tank 202. Optionally, gas flows through pipe 204 towards vacuum source 206. In some embodiments, the tank is sealed, so that the vacuum induced within pipe 200 is not affected by the passing of its continuing pipes 201 and 204 through tank 202.

User Interface and Modes of Operation

In some embodiments, a workstation 12 of the colon cleaning system, for example comprising controller 300, comprises a user interface 301. In some embodiments, user interface 301 is configured as a button panel. Additionally or alternatively, user interface 301 comprises a screen and/or a keyboard. Optionally, the user interface provides for entering patient related data, a treatment plan, and/or other data for carrying out the procedure.

In some embodiments, an operation mode of the system is selected, for example by a user such as a physician, through user interface 301. Alternatively, the operation mode is selected automatically. Optionally, the automatic selection is performed according to predefined parameters, and/or according to patient data and/or treatment conditions. Optionally, the operation mode is modified during the procedure, for example based on real time feedback. Feedback may be provided, for example, by a pressure indication from the sensor, an image provided by a visualizing device, an amount of fluid and/or fecal matter collected within tank 202 or any other indication thereof.

The following is a list of exemplary modes of operation. It is noted that the system is not limited to these modes of operation, and may comprise other operational modes or a combination thereof:

(a) a mode in which the ancillary vacuum module is restricted (that is, a mode in which a pressure differential is not applied to the pipe of the ancillary vacuum module), and vacuum is induced solely within the working channel. Optionally, this configuration is obtained by maintaining solenoid valve 209 closed at all times, so that vacuum is not induced in separate vacuum pipe 200. In some cases, for example for safety purposes, valve 209 is automatically closed, for example in cases of electrical power loss, to prevent unwanted application of vacuum.

(b) a mode in which activation of the vacuum control valve 122, for example as explained above, generates vacuum within separate vacuum pipe 200, optionally according to a pressure level sensed at conduit 220A.

(c) a mode in which the separate vacuum module is activated independently of the working channel and/or the vacuum control valve. In some embodiments, the separate vacuum module is activated by an additional user interface, for example comprising a foot pedal, a button or valve.

Exemplary Pressure Ranges and Operation Parameters

In some embodiments, vacuum source 206 (e.g. a vacuum pump) is calibrated to provide suction so that a pressure level in one or more pipes 208 ranges between 600-800 mbar, for example 650, 700, 750 mbar Optionally, secondary vacuum regulator 205 is configured for modifying the applied vacuum pressure so that the pressure within pipe 204 (which is connected, optionally through tank 202, to separate vacuum pipe 200) ranges between 400-600 mbar, for example 450, 500, 600 mbar or intermediate, higher or lower pressure levels. Optionally, vacuum regulator 212 is configured for modifying the applied vacuum pressure so that the pressure within conduit 220A (assuming that valve 122 is in its closed configuration) ranges between 200-300 mbar, for example 220, 250, 270 mbar 450, 500, 600 mbar or intermediate, larger or smaller pressure levels.

In some embodiments, separate vacuum pipe 200 is configured to evacuate liquid, such as water, at a rate ranging between 1500-1900 cc/min, for example, 1600, 1700, 1800 cc/min or intermediate, larger or smaller rates.

In some embodiments, vacuum is provided in pulses. Optionally, a duration of a pulse ranges between, for example, 1-100 seconds, such as 10 seconds, 50 seconds, 75 seconds or intermediate, longer or shorter periods. In some embodiments, a time interval between the pulses ranges between, for example, 1-1000 seconds, such as 10 seconds, 300 seconds, 700 seconds or intermediate, longer or shorter time intervals.

A Pressure Sensor Configured for Measuring Pressure Within the Colon

In some embodiments, one or more pressure sensors 4000 are configured at portion 125 of the working channel, for example coupled to outer tube 14. Optionally, pressure sensor 4000 is configured for detecting a pressure level within colon 1. Optionally, a signal from sensor 4000 is received by controller 300. In some embodiments, the parameters of the vacuum induced in separate vacuum pipe 200 are determined according to the colon pressure indication. Optionally, the vacuum is induced according to differences between the pressure indication provided by sensor 211 at conduit 220A and the pressure indication provided by sensor 4000 within the colon.

Figure 5A:
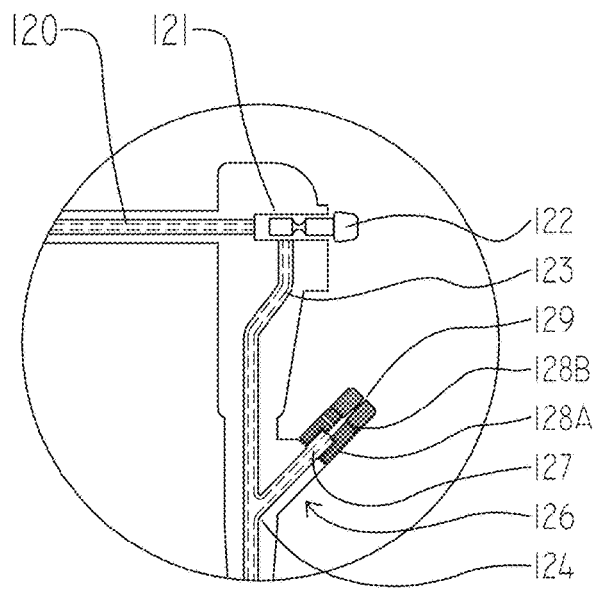
FIGS. 5A-5C illustrate an exemplary embodiment of a Y-junction of a colonoscope, and a blocking element insertable into the working channel, according to some embodiments of the invention.
Figure 5B:
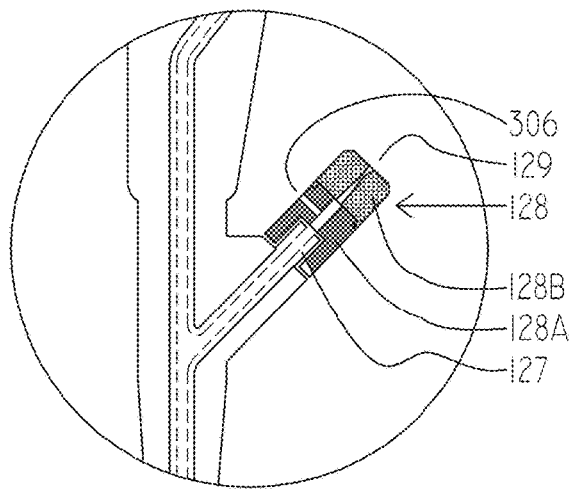
Figure 5C:
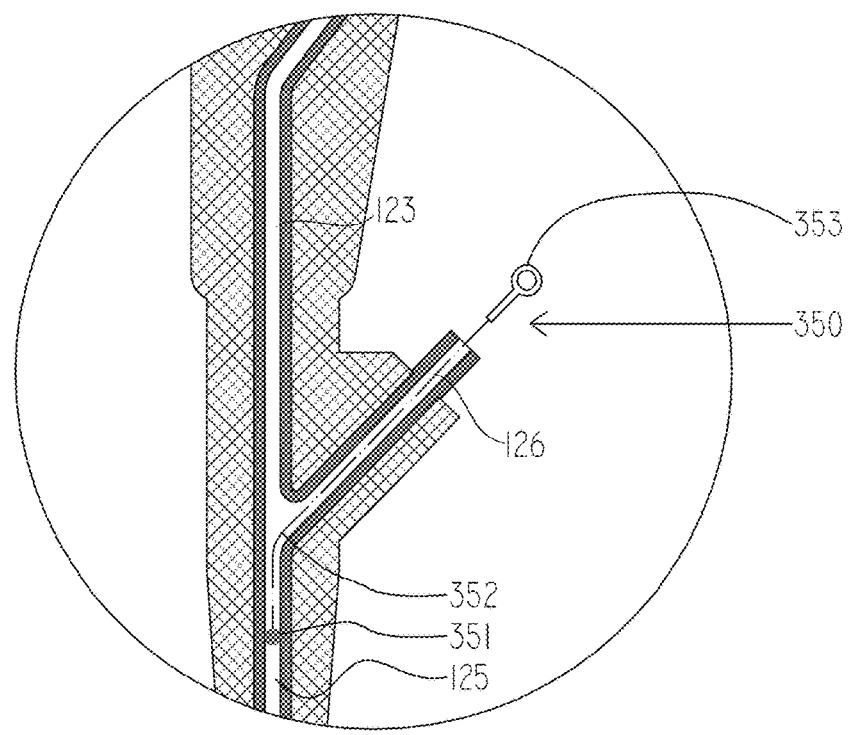

FIGS. 5A-C are an exemplary embodiment of a Y-junction of a colonoscope (FIGS. 5A-5B), and a blocking element insertable through the Y-junction (FIG. 5C), according to some embodiments of the invention.

In some embodiments, the colon cleaning system comprises a Y-junction 124. Optionally, a first branch extending from the Y-junction comprises working channel portion 123, and a second branch extending from the Y-junction comprises branch 126.

In some embodiments, branch 126 is used for insertion of tools into the working channel, for example tools for collecting tissue for a biopsy or for removal of polyps from the colon, such as scissors or a clamping implement. In some embodiments, an opening 127 of branch 126 is covered by a cap 128. Optionally, cap 128 comprises a base portion 128, which, in some embodiments, is fixedly connected to branch 126, and a removable portion 128B. Optionally, removable portion 128B is hingedly connected to base 128A. Additionally or alternatively, removable portion 128B is connected to base 128A by a threaded connection. In some embodiments, when portion 128B is removed, vacuum is relieved and no or small, insignificant vacuum is generated within the working channel. Respectively, when portion 128B is positioned on branch 126, vacuum can be generated within the working channel, for example when valve 122 is pushed into its housing, allowing a connection between pipe 120 and working channel portion 123.

In some embodiments, portion 128B comprises an orifice 129, through which a tool can be inserted. Optionally, portion 128B is formed of a material flexible enough to fit closely around the inserted tool, so that even when vacuum is generated a user can maneuver the tools within the colon substantially without interrupting the evacuation of matter from the colon. For example, portion 128B can be formed of rubber, plastic, silicon. Optionally, once a tool is removed from orifice 129, the orifice walls spring back closer to each other, reducing a diameter of the opening.

In some embodiments, as shown in the enlarged view of FIG. 5B, base cap portion 128A comprises an air vent 306. Optionally, a diameter of air vent 306 is small enough so that it does not affect the breaching of vacuum within the working channel.

A Blocking Element Insertable Into the Working Channel

FIG. 5C shows an exemplary blocking device insertable into the working channel, according to some embodiments in the invention. In some embodiments, blocking element 351, for example formed as a ball, a cork, or any other type of plug is inserted into working channel portion 125. Optionally, blocking element 351 comprises an inflatable balloon. Optionally, blocking element 351 comprises a radially expandable disc, or other element configured for obstructing a portion of the working channel. In some embodiments, the blocking element is inserted through branch 126 of the Y-junction. Optionally, cap 128 is removed prior to insertion. Alternatively, blocking element 351 is squeezed through orifice 129 to enter the working channel. In some embodiments, a wire or string 352 is coupled to element 351 to enable its manipulation. Optionally, a proximal end of wire 352 is coupled to a handle 353, positioned externally to the body. Optionally, a geometry and/or size of handle 353 is suitable (for example, large enough) to prevent the handle from entering branch 126.

In some embodiments, by insertion of element 351 into the working channel, element 351 forms a barrier between portions 123 and 125 of the working channel. Optionally, the barrier prevents vacuum from breaching through distal portion 125 of the working channel, where fecal matter may exist. Additionally or alternatively, the barrier provides for activating the separate vacuum module independently of the working channel. Optionally, the blocking element hermetically seals portion 125 of the working channel.

In some embodiments, for example in a situation in which both the working channel and the separate vacuum pipe are clogged, the pressure levels may be affected by the clogging, and the proper functioning of the system may be interrupted. In such a situation, insertion of element 351 to portion 125 of the working channel when valve 122 is pushed-in, may cause the pressure in portion 123 of the working channel to reach a level it would normally reach during standard operation (i.e. when the working channel and separate vacuum pipe are not clogged), thereby imitating normal operating conditions and optionally preventing unpredictable behavior of the system. The pressure indication at the conduit (such as conduit 220A described herein above) may not be affected (due to the "normal" pressure level at portion 123 of the working channel) and will indicate, for example, a relatively low pressure, signaling the controller to generate vacuum within the external vacuum pipe for evacuating fecal matter and releasing the clogging.

FIG. 6 shows an exemplary configuration of a colon cleaning system comprising an ancillary vacuum module, according to some embodiments of the invention. In this configuration, two collection tanks 202 and 210B are incorporated in the system. In some embodiments, tank 202 is positioned along the vacuum supply line leading to separate vacuum pipe 200, to collect fluid and/or fecal matter evacuated by vacuum pipe 200. In some embodiments, tank 210B is positioned between conduit 220A and a continuing conduit 210 extending distally to conduit 220A, to collect fluid and/or fecal matter evacuated by the working channel. Optionally, tank 202 and/or tank 210B are configured for separating liquid from gas. Additionally or alternatively, tank 202 and/or tank 210B collect fecal matter 2. Optionally, each or both of the tanks are sealed so that a constant air gap is maintained between the lid of the tank and a surface of the collected fluid. Optionally, by maintaining this constant air gap, the pressure levels and/or vacuum induced are not affected by passing through the tank.

Figure 7A:
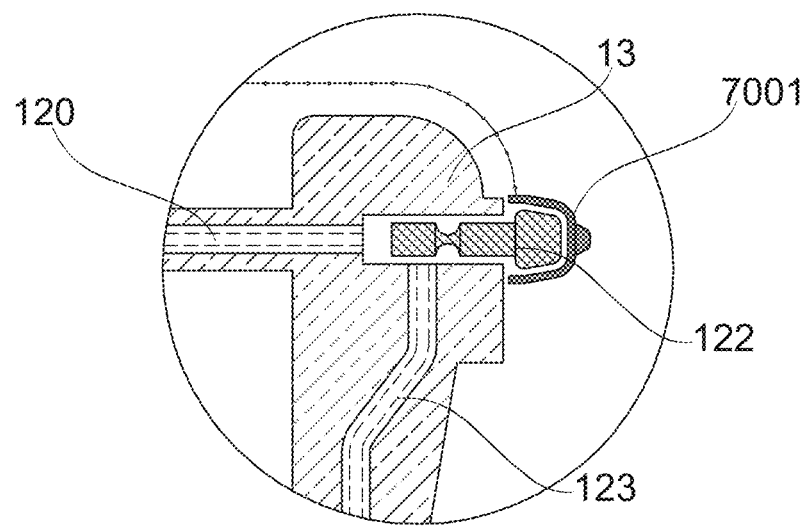
FIGS. 7A-7B illustrate various embodiments of a vacuum control valve, according to some embodiments of the invention.
Figure 7B:
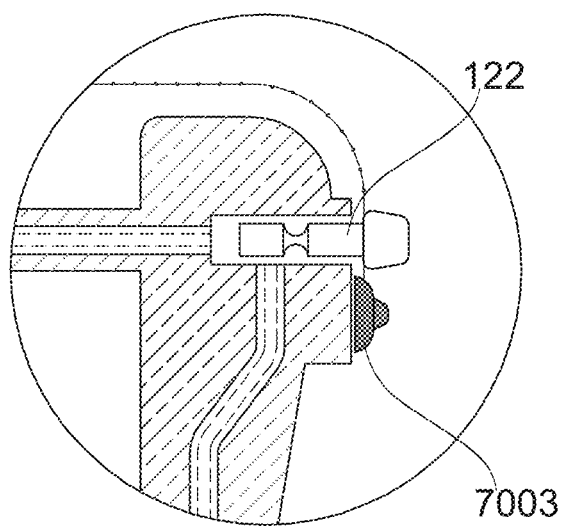

FIGS. 7A-B are exemplary configurations of a vacuum valve 122, according to some embodiments of the invention. As referred to herein above, the vacuum valve may be used for permitting induction of vacuum within the working channel, and/or for activating the induction of vacuum within the separate vacuum pipe.

FIG. 7A shows an embodiment of a self-release valve. Valve 122 is encased in an external pushbutton 7001. Optionally, pushbutton 7001 is pressed to advance valve 122 into its housing 13. Optionally, pushbutton 7001 is configured for springing back to a non-pushed configuration once force is removed, and by being coupled to valve 122 the valve is caused to return to a pulled back state. Optionally, vacuum is induced in the pushed-in state, where valve 122 permits a connection between portion 123 of the working channel and pipe 120. Optionally, pushbutton 7001 can be pushed in gradually, increasing the intensity of the applied vacuum upon advancement.

FIG. 7B shows an embodiment in which an additional button 7003 is provided, for example adjacent valve 122, to separate between the functions of applying vacuum and ceasing the vacuum. Optionally, button 7003 is mechanically and/or electrically coupled to valve 122, so that operation of button 7003 determines the positioning of valve 122. For example, button 7003 can be pressed for activating vacuum, causing valve 122 to advance to a pushed-in state, and valve 122 can be pulled back to cease the vacuum, or vice versa.

Figure 8A:
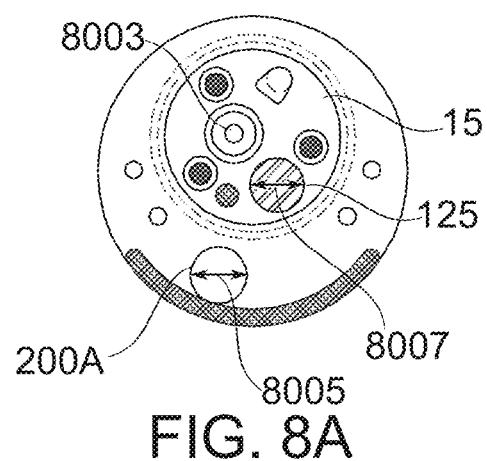
FIGS. 8A-8B illustrate a front view and a side view of a distal portion of the colonoscope and the separate vacuum pipe, according to some embodiments of the invention.
Figure 8B:
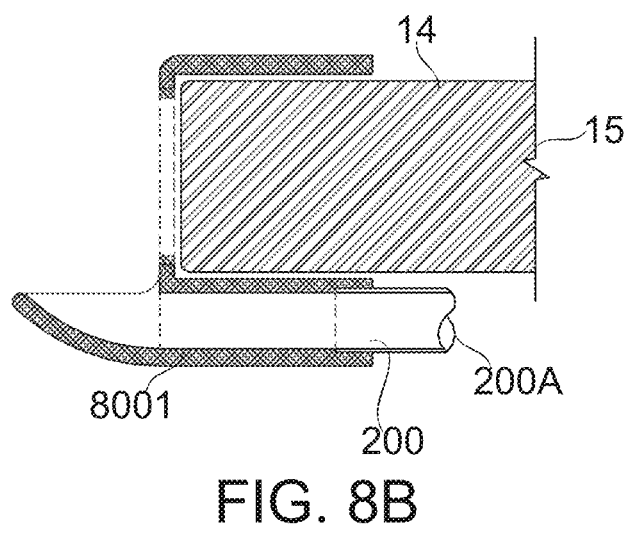

FIGS. 8A-B are a front view (FIG. 8A) and a side view (FIG. 8B) of a distal end of a colonoscope and a distal end of a separate vacuum pipe, according to some embodiments of the invention.

In some embodiments, opening 200A of the separate vacuum pipe is positioned in proximity to opening 15 of the colonoscope, for example positioned at a radial distance ranging between 0.1-30 mm, such as 0.7 mm, 5 mm, 15 mm, 25 mm or intermediate, longer or shorter distances from a periphery of the colonoscope at distal end 15.

In some embodiments, at least the distal portions of the colonoscope 14 and separate vacuum pipe 200 are held together by a common head housing 8001. Optionally, head housing 8001 aligns the openings of both tubes (i.e. the colonoscope and the separate vacuum pipe) with respect to each other. In some embodiments, the openings are positioned at an axial distance from each other, for example one positioned distally to the other, for example at a distance of 1 mm, 5 mm, 10 mm or intermediate, longer or shorter distances from each other.

In some embodiments, vacuum pipe 200 and colonoscope 14 are coupled to each other at least along a portion of their lengths, for example along 40%, 60%, 80% or intermediate, larger or smaller percentages of the length of vacuum pipe 200. Optionally, vacuum pipe 200 is attached to colonoscope 14 by one or more of tapes, attachment rings, an external flexible tube, clips, glue, other fixation elements or a combination thereof.

The front view of colonoscope's 14 distal opening 15, shown at FIG. 8A, includes, for example, a distal opening of working channel 125, an imaging device 8003 and/or associated illumination, and/or other tools insertable into the colonoscope. Opening 200A of separate vacuum pipe 200 is positioned adjacent opening 15 of the colonoscope. In some embodiments, a diameter 8005 of opening 200A is equal to a diameter 8007 of the opening of working channel 125. Alternatively, diameter 8005 is smaller than or larger than a diameter 8007 of the working channel. Optionally, a diameter of separate vacuum pipe 200 ranges between, for example, 2-10 mm, such as 4 mm, 6 mm, 8 mm or intermediate, longer or shorter diameters.

Figure 9:
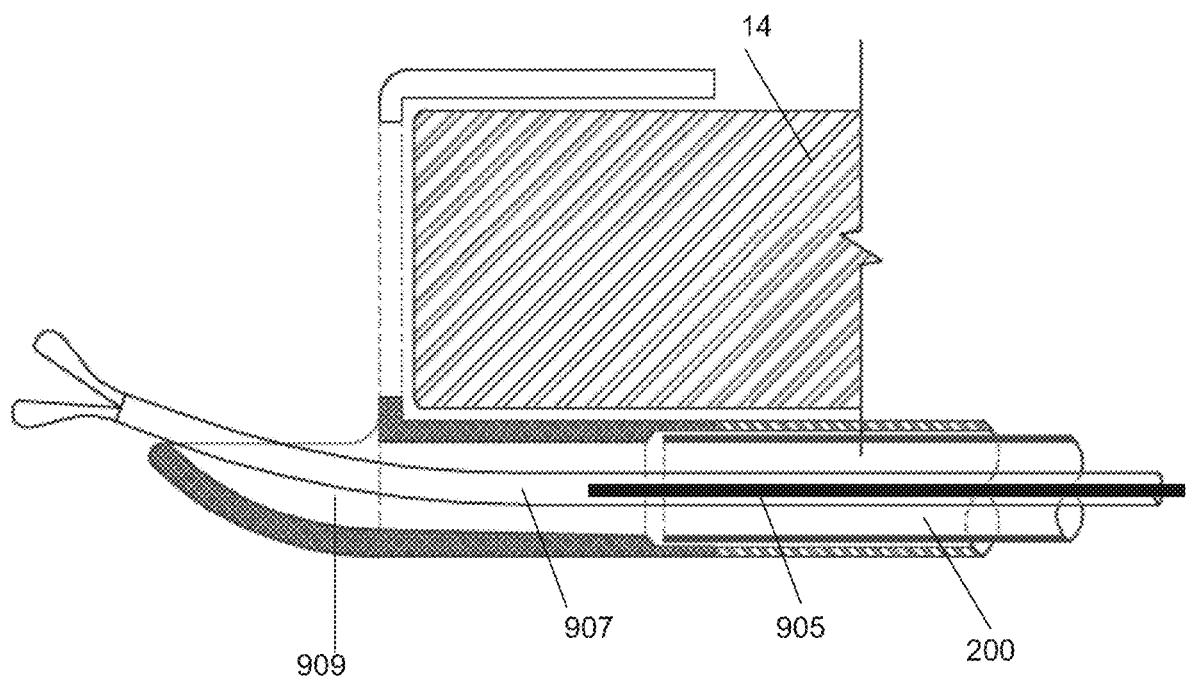
FIG. 9 schematically illustrates of a separate pipe configured for delivery of one or more tools into the intestinal tract, according to some embodiments of invention.

FIG. 9 shows an embodiment of a separate pipe 200 configured for delivery of one or more tools 905 into the colon. Optionally, pipe 200 extends adjacent at least a portion of a colonoscope 14.

In some embodiments, a tube 907 is passed within pipe 200, for example extending along its length, and tool 905 is delivered through tube 907. Exemplary tools may include polyp removal tools.

In some embodiments, tube 907 is formed of a rigid material, for example formed of plastic such as PVC. Optionally, tube 905 is stiffer than pipe 200. A potential advantage of passing tool 905 within tube 907 as opposed passing tool 905 directly within pipe 200 (i.e. without tube 907) may include reducing or preventing damage to the walls of pipe 200.

In some embodiments, pipe 200 is a separate vacuum pipe, for example as described hereinabove. Optionally, vacuum is not applied when tool 905 is inserted through pipe 200. Alternatively, vacuum is applied through pipe 200, for example through lumen 909 of the pipe, without affecting the lumen of tube 907. Optionally, vacuum is applied in parallel to the delivery of tool 905, for example by positioning a valve at the entrance to tube 907 for preventing the vacuum to breach through the tube.

In some embodiments, pipe 200 is used for insertion of tools once a user such as a physician positions the distal openings of colonoscope 14 and pipe 200 at a desired location within the intestinal tract, for example in proximity to the cecum.

In some embodiments, tool 905 can be passed over a guide wire that is passed through tube 907.

A potential advantage of a pipe 200 configured for providing vacuum and/or for delivery of tools into the colon may include providing a secondary pathway leading into the colon, to be used in a separate or simultaneous manner with the working channel.

Figure 10:
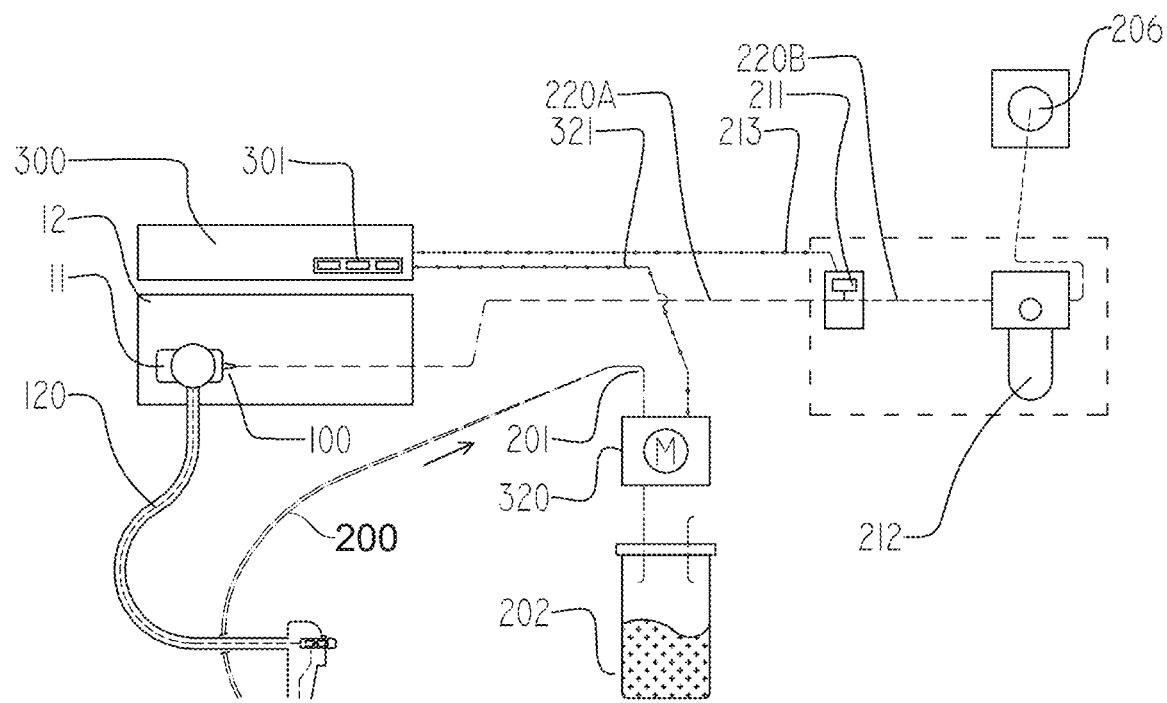
FIG. 10 illustrates a colon cleaning system comprising an additional vacuum source to be used with a separate vacuum pipe, according to some embodiments of the invention.

FIG. 10 is an exemplary configuration of a colon cleaning system comprising a vacuum source, for example configured as vacuum motor 320. In some embodiments, a colon cleaning system comprises two or more vacuum sources, for example one to be used with the working channel, such as vacuum source 206, and one to be used with separate vacuum pipe 200, such as vacuum motor 320.

In some embodiments, vacuum motor 320 is connected to controller 300. In some embodiments, vacuum motor 320 is adapted for inducing vacuum in separate vacuum pipe 200 (shown only in part in this figure), for example through secondary pipe 201. In some embodiments, vacuum motor 320 is activated based on a signal received from controller 300, for example according to a pressure related indication provided by sensor 211. In some embodiments, fluid and/or gas and/or fecal matter are evacuated by pipe 200 (leading to pipe 201), and are passed by motor 320 to reach tank 202.

In some embodiments, controller 300 is configured to operate vacuum source 206 and/or vacuum motor 320 and/or vacuum regulator 212 based on a signal received from one or more of the listed components. For example, vacuum motor 320 can be activated to induce vacuum within pipe 200 when vacuum regulator 212 is set to prevent vacuum from breaching through conduit 220A.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A colon cleaning system configured for coupling to at least one vacuum source, the system comprising:
   a working channel of a colonoscope;
   wherein the working channel is configured to be functionally coupled to the at least one vacuum source so that the working channel is configured for the evacuation of fecal matter from a colon of a human body when inserted into said colon;
   a separate vacuum pipe configured to be functionally coupled to the at least one vacuum source, the separate vacuum pipe being positioned outside the colonoscope and along an extent of the separate vacuum pipe which is also positioned alongside a portion of said working channel configured for insertion into said colon;
   a conduit configured to remain outside the human body when the working channel is inserted into said colon, said conduit connected to said working channel; and
   a sensor positioned in said conduit and configured to provide an indication related to pressure within at least a segment of said working channel; and
   a controller configured for controlling at least one parameter of a vacuum induced in said separate vacuum pipe from the at least one vacuum source to a strength strong enough to evacuate, through an opening of the separate vacuum pipe positioned alongside the portion of the working channel, at least one of fecal matter and fluid from the colon when the separate vacuum pipe is inserted into said colon alongside the working channel, said at least one parameter being determined according to said pressure-related indication provided by said sensor;
   said controller comprising a user interface through which a user can select an operation mode, said system configured to allow selection of any of the following operation modes;
   (a) a mode in which induction of vacuum in said separate vacuum pipe from said at least one vacuum source is restricted and vacuum is induced solely in said working channel;
   (b) a mode in which said controller determines said at least one parameter of the induced vacuum in said separate vacuum pipe from said at least one vacuum source according to said pressure-related indication provided by said sensor; and
   (c) a mode in which vacuum is induced in said separate vacuum pipe from said at least one vacuum source independently of said pressure-related indication.

2. The system according to claim 1, wherein said at least one parameter of said induced vacuum from the at least one vacuum source includes at least one of timing, intensity, and frequency.

3. The system according to claim 1, wherein said controller is configured to control at least one of an intensity and timing of said induced vacuum in said separate vacuum pipe from the at least one vacuum source.

4. The system according to claim 1, wherein said functional coupling of the vacuum source to the working channel comprises the conduit extending between said working channel and said vacuum source.

5. The system according to claim 1, wherein said sensor detects at least one of a change in pressure, and an absolute pressure.

6. The system according to claim 1, wherein the at least one parameter of the vacuum provided in the separate vacuum pipe from said at least one vacuum source is controlled by a vacuum regulator controlled by the controller.

7. The system according to claim 6, wherein said at least one parameter of the vacuum is controlled according to a difference between said pressure-related indication and a predefined pressure indication profile.

8. A colon cleaning system configured for coupling to at least one vacuum source, the system comprising:
   a working channel of a colonoscope;
   wherein the working channel is configured to be functionally coupled to the at least one vacuum source so that the working channel is configured for the evacuation of fecal matter from a colon of a human body when inserted into said colon;
   a separate vacuum pipe configured to be functionally coupled to the at least one vacuum source, the separate vacuum pipe being positioned outside the colonoscope along an extent of the separate vacuum pipe which is also positioned alongside a portion of said working channel configured for insertion into said colon;
   a conduit configured to remain outside a human body when the working channel is inserted into said colon of said human body, said conduit connected to said working channel; and
   a controller configured for controlling at least one parameter of a vacuum induced in said separate vacuum pipe from the at least one vacuum source to a strength strong enough to evacuate, through an opening of the separate vacuum pipe positioned alongside the portion of the working channel, at least one of fecal matter and fluid from the colon when the separate vacuum pipe is inserted into said colon alongside the working channel, said at least one parameter based on a level of pressure in said conduit;

said controller comprising a user interface through which a user can select an operation mode, said system configured to allow selection of any of the following operation modes:

(a) a mode in which induction of vacuum in said separate vacuum pipe from said at least one vacuum source is restricted and vacuum is induced solely in said working channel;

(b) a mode in which said controller determines said at least one parameter of the induced vacuum in said separate vacuum pipe from said at least one vacuum source based on a level of pressure in said conduit; and (c) a mode in which vacuum is induced in said separate vacuum pipe from said at least one vacuum source independently of a level of pressure in said conduit.

9. The system according to claim 1, wherein the at least one parameter of the vacuum provided in the separate vacuum pipe from said at least one vacuum source is controlled by a pump controlled by the controller.

10. The system according to claim 1, wherein the at least one parameter of the vacuum provided in the separate vacuum pipe from said at least one vacuum source is controlled by a valve controlled by the controller.

\* \* \* \* \*